United States Patent [19]

Attali et al.

[11] Patent Number: 4,805,156

[45] Date of Patent: Feb. 14, 1989

[54] SYSTEM FOR ACOUSTICALLY DETERMINING THE QUALITY OF THE CEMENT BOND IN A CASED BOREHOLE

[75] Inventors: George Attali, Houston; James R. Birchak, Spring; Robert A. Lester, Houston, all of Tex.

[73] Assignee: Western Atlas International, Inc., Houston, Tex.

[21] Appl. No.: 910,076

[22] Filed: Sep. 22, 1986

[51] Int. Cl.$^4$ .............................................. G01V 1/00
[52] U.S. Cl. ...................................... 367/35; 367/28; 181/105
[58] Field of Search ...................... 367/25, 27, 28, 30, 367/31, 33, 35, 69, 75, 911, 912; 181/102–108, 111, 112; 166/253; 175/50; 33/302

[56] References Cited

U.S. PATENT DOCUMENTS

| | | | |
|---|---|---|---|
| 3,512,407 | 5/1970 | Zill | 367/25 X |
| 3,781,784 | 12/1973 | Desbrandes | 367/30 |
| 3,811,529 | 5/1974 | Crawford | 181/104 |
| 4,255,798 | 3/1981 | Havira | 181/105 X |
| 4,293,934 | 10/1981 | Herolz et al. | 367/31 X |
| 4,551,823 | 11/1985 | Carmichael et al. | 367/35 |
| 4,607,352 | 8/1986 | Seeman et al. | 367/35 |
| 4,641,724 | 2/1987 | Chow et al. | 367/28 X |
| 4,709,357 | 11/1987 | Maki, Jr. | 367/35 |

FOREIGN PATENT DOCUMENTS

1185350 4/1985 Canada .................................. 367/35

Primary Examiner—Brian S. Steinberger
Attorney, Agent, or Firm—Browning, Bushman, Zamecki & Anderson

[57] ABSTRACT

The present invention is directed to an apparatus and method for obtaining azimuthally dependent measurements for evaluating the casing cement bond quality and, more particularly, for detecting and specifically locating channels or fissures between the casing and cement. The quality of the bond behind one or more arcs of known location on the casing is determinable by the present invention. The apparatus and method of the present invention employ a plurality of sonic transducers disposed in near contact with the casing in defined segmented locations about or around the exterior surface of a downhole tool. The transducers are arranged in a plurality of arrays, each array comprising four transducers, two transmitting and two receiving transducers, disposed along a single arc about or around the exterior of the tool. The transducers are arranged so that two adjacent transducers in each array perform the same function in the array so that the bond quality between the similarly functioning and adjacent transducers is determined. The sets of arrays of transducers provide determinations in a continuous and complete loop around the casing. The casing cement bond quality is determined by measuring the attenuation of the compression wave from a pulsed acoustic wave traveling along the arcs of the helices. The apparatus and method of the present invention are also useful for making azimuthally dependent measurements in hard formations to detect fractures in uncased boreholes. When detecting fractures, the attenuation of the shear wave rather than the compression wave is measured.

45 Claims, 9 Drawing Sheets

SYSTEM FOR ACOUSTICALLY DETERMINING THE QUALITY OF THE CEMENT BOND IN A CASED BOREHOLE

BACKGROUND OF THE INVENTION

1. Field of the Invention

The present invention generally relates to an apparatus and method useful for determining the quality of the cement bond between a wall of a borehole penetrating an earth formation and a casing cemented therein. The quality of the bond behind one or more arcs of known location on the casing is determined by the present invention. The present invention further comprises an improved method of steering or directing the acoustic signal to maximize the signal transmitted and/or received. The present invention comprises an apparatus and method employing a plurality of sonic transducers in defined segmented locations for making the desired measurements.

2. Description of the Background

In the oil and gas industry, wells are completed by setting a string of pipe or casing in the borehole and filling the annulus between the pipe or casing and the borehole with cement. This cementing operation separates the various formation zones, and particularly separates the productive oil and gas bearing formations from non-productive formations such as water-bearing formations. Once separated by the cementing operation, only the desired oil and gas bearing formations are perforated for production. Failure or incompleteness of the cement bond likely will result in incomplete separation between the various formations. Migration of fluids under pressure through voids or cracks appearing in the cement between the casing and borehole wall causes contamination of the fluids of one zone with the fluids of another zone. This contamination is particularly undesirable where fluids from water-bearing strata migrate into fluids in a producing zone. This migration typically results in decreased production of hydrocarbon fluids and increased production of non-desirable fluids and contamination of equipment. These results often cause serious financial loss and may even cause a well to become non-commercial.

Accordingly, the desirability of accurately determining the quality of the cement bond between a casing and a wall of a borehole has long been a goal of those associated with the oil and gas industry. A "good bond" produces the desired separation of zones and is achieved with good adhesion, although micro-fissures or a micro-annulus may be present.

Many prior systems have been developed for investigating the bond quality between a casing and a borehole wall. Prior systems for inspecting the cement bond in wells in the oil and gas industry have included conventional acoustic cement bond systems employing acoustical energy in a variety of devices and methods. In fact, such a system is described and claimed in U.S. Pat. No. 4,255,798 to Havira which employs an acoustic pulse echo technique for investigating the quality of the cement bond to a casing and the thickness of a casing located in a borehole. Further, the Havira patent lists and describes in columns 2–7 a plurality of patents and articles describing in detail many prior art systems for evaluating cement bond quality using acoustic energy. The Havira patent and its extensive description of these prior systems are incorporated herein by reference.

However, these prior acoustic systems typically suffer from one or two major drawbacks. Many of these prior systems merely provide an average indication of the bond quality about the entire circumference of the casing at the measured depth within the borehole. Accordingly, the investigator using such systems cannot determine the specific azimuthal location about the borehole where a channel may be located. In fact, the investigator cannot distinguish a troublesome channel from several small fissures. Other systems which do provide azimuthal scanning measure the bond condition at only specific points around the circumference and give no indication of the bond condition over the arc between those points.

Accordingly, there has been a long felt but unfulfilled need within the oil and gas industry for an effective apparatus and method useful for providing an inspection system for determining bond quality in specific, azimuthally located arcs of a cemented casing.

SUMMARY OF THE INVENTION

The present invention provides a new and improved apparatus and method for determining the quality of a bond between the wall of a borehole penetrating an earth formation and a casing cemented therein. The acoustic logging tool and method of the present invention provide an indication of the bond quality behind an arc of the casing defined by two circumferentially separated points at a known depth and orientation within the borehole. The apparatus and method of the present invention provide information on the integrity of the bond between the casing and the cement as a function of azimuth about the casing periphery.

In a simple embodiment, an acoustic logging tool useful with the present invention comprises a sonde including means for securing the sonde to a wireline. Disposed peripherally about or around the exterior surface of the sonde are a plurality of transducers for transmitting and receiving acoustic pulse signals into a casing cemented in a borehole. The transducers are arranged and coupled to appropriate electrical circuitry to provide a means for operating the transducers in a plurality of arrays. Each array comprises four transducers disposed along a single arc defined by one or more helices extending about or around the exterior of the sonde. Each array comprises first and second transducers capable of transmitting and first and second transducers capable of receiving an acoustic pulse signal. Finally, the transducers of each array are disposed so that the transducers of an adjacent pair of transducers in each array perform the same function in the array. The preferred transducer pattern in the arrays is $T_1$-$R_1$-$R_2$-$T_2$. Other acceptable transducer patterns in the arrays include $R_1$-$T_1$-$T_2$-$R_2$ and $T_1$-$T_2$-$R_1$-$R_2$. These arrays permit a determination of the bond quality between the adjacent transducers performing the same function in the array. The arrays are preferably disposed along the pitch of one or more helices along the axis of the tool.

The present invention further provides a new and improved transducer configuration for transmitting maximum strength acoustic signals and receiving minimum strength acoustic signals to improve the detection limits for a bond quality tool. The improved configuration is useful in the apparatus and method of the present invention for determining the quality of a bond between the wall of a borehole penetrating an earth formation and a casing cemented therein.

The improved transducer configuration of the present invention provides a means for maximizing the signal transmitted or received along the arc of investigation about the surrounding casing or borehole. In the improvement of the present invention, each transducer comprises at least two sequentially operated transducer elements. In the preferred embodiment, each transducer comprises a pair of square transducer elements placed along the axis of the tool or borehole, having dimensions one-half the acoustic wave length and disposed so that the edges of the square are perpendicular to the line of transmission along the pitch of the helix and most preferably at 45° angles to the tool axis. The individual elements of these transducers are sequentially operated in order to maximize the signal strength transmitted along the pitch of the helix, most preferably at ±45° to the tool or casing axis and directed toward the receiving transducers. Use of transducer elements of this improved configuration maximizes the signal strength along the arc of investigation and improves the accuracy of bond quality determination.

The logging tool further comprises means for generating a first acoustic pulse signal from the first transmitting transducer and a second acoustic pulse signal from the second transmitting transducer and means for measuring the maximum amplitude of a portion of the first signal received at each of the first and second receiving transducers and the maximum amplitude of a portion of the second signal received at each of the first and second receiving transducers. Finally, the tool comprises means for determining the time for either of the acoustic pulse signals to travel between the adjacent pair of similarly functioning transducers which define the first and second circumferentially separated points between which the bond quality is determined.

In electrical communication with the above measuring and determining means is means for computing the rate of attenuation of the acoustic pulse signals between the adjacent pair of similarly functioning transducers based on the measured maximum amplitudes and travel time. In more preferred embodiments, the transducers are equidistantly spaced about an elongated housing having a longitudinal axis. In an exemplary configuration, five transducers equidistantly spaced about the housing in a single plane perpendicular to the longitudinal axis of the housing produce five different transducer arrays providing measurements of bond quality behind each of five segments of 72° each. Because of geometry problems encountered in disposing the transducers about the housing, particularly where smaller measurement arcs are desired, more preferred embodiments provide for helical disposition of the transducers. In a presently preferred embodiment, nine transducers are disposed equidistantly along a single helix of 480° providing measurement about six segments each of 60°. Alternative preferred embodiments include twelve transducers disposed in two helices of six transducers each, the two helices being displaced 180° about the housing. Another alternative embodiment comprises twelve transducers disposed in three helices of four transducers each, each helix being displaced 120° about the housing. Adjacent transducers are preferably separated by a distance at least as great as $3\lambda$ where $\lambda$ is the wavelength of the acoustic pulse signals of the system or by a distance at least as great as $12t_h$ where $t_h$ is the thickness of the casing of the borehole.

A system in accord with the present invention further includes means for displaying the rate of attenuation and for comparing the computed attenuation with an attenuation indicative of a good bond.

The method of the present invention is useful for detecting the quality of a cement bond behind a wall of a borehole penetrating an earth formation. The method comprises the steps of transmitting a first acoustic compression wave through the casing along an arc defined by first and second circumferentially separated points so that the wave arrives at the first point before arriving at the second point. The improvement of the present invention comprises enhancing the strength of the transmitted and received signal by sequentially activating a pair of transducer elements comprising each transducer. The transducer elements each include a straight, leading face perpendicular to the arc of investigation on a line toward the receiver. Sequential activation of these elements with appropriate time delay maximizes the transmitted and received signal strength. The maximum amplitude of the wave is measured at both the first and second points together with the time for the wave to travel between the first and second points. The method further comprises transmitting a second acoustic compression wave through the casing and along the arc and measuring the maximum amplitude of the second wave received at each of the first and second points. The method further comprises computing the rate of attenuation for the acoustic compression wave between the first and second points from the four measured amplitudes and the measured travel time and displaying the rate of attenuation as an indication of the quality of the cement bond. Alternatively, or additionally, the computed attenuation is compared to the attenuation for a good bond or a bond of known quality. If the depth and orientation within the borehole is not previously known, the method further comprises measuring the azimuth of the borehole and the depth within the borehole.

The apparatus and method of the present invention provide a means for accurately determining the quality of the cement bond behind an arc of the casing in a cemented borehole. The apparatus and method of the present invention provide a means for precisely locating channels, fissures and other imperfections in the cement behind the casing. These and other meritorious features and advantages of the present invention will be more fully appreciated from the following detailed description and claims.

BRIEF DESCRIPTION OF THE DRAWINGS

Other features and intended advantages of the present invention will be more readily apparent by the references to the following detailed description in connection with the accompanying drawings, wherein.

While the invention will be described in connection with the presently preferred embodiment, it will be understood that it is not intended to limit the invention to this embodiment. On the contrary, it is intended to cover all alternatives, modifications and equivalents as may be included in the spirit of the invention as defined in the appended claims.

DETAILED DESCRIPTION OF THE PREFERRED EMBODIMENT

The present invention is directed to an apparatus and method useful for determining the quality of a bond between a wall of a borehole penetrating an earth formation and a casing cemented therein. This determination is made between two circumferentially separated points on an arc of the casing. The apparatus and method of the present invention employs a plurality of transducers for transmitting and receiving an acoustic pulse compression wave through the casing between the two circumferentially separated points. Measurement of the maximum amplitude of a selected portion of the signal received by transducers located at the two separated points and the travel time therebetween for each of two such acoustic pulse compression waves permits calculation of the rate of attenuation of the acoustic pulse signal between the two points and comparison with the attenuation between similar points for a good bond or a bond of known quality.

Figures 1, 1A:
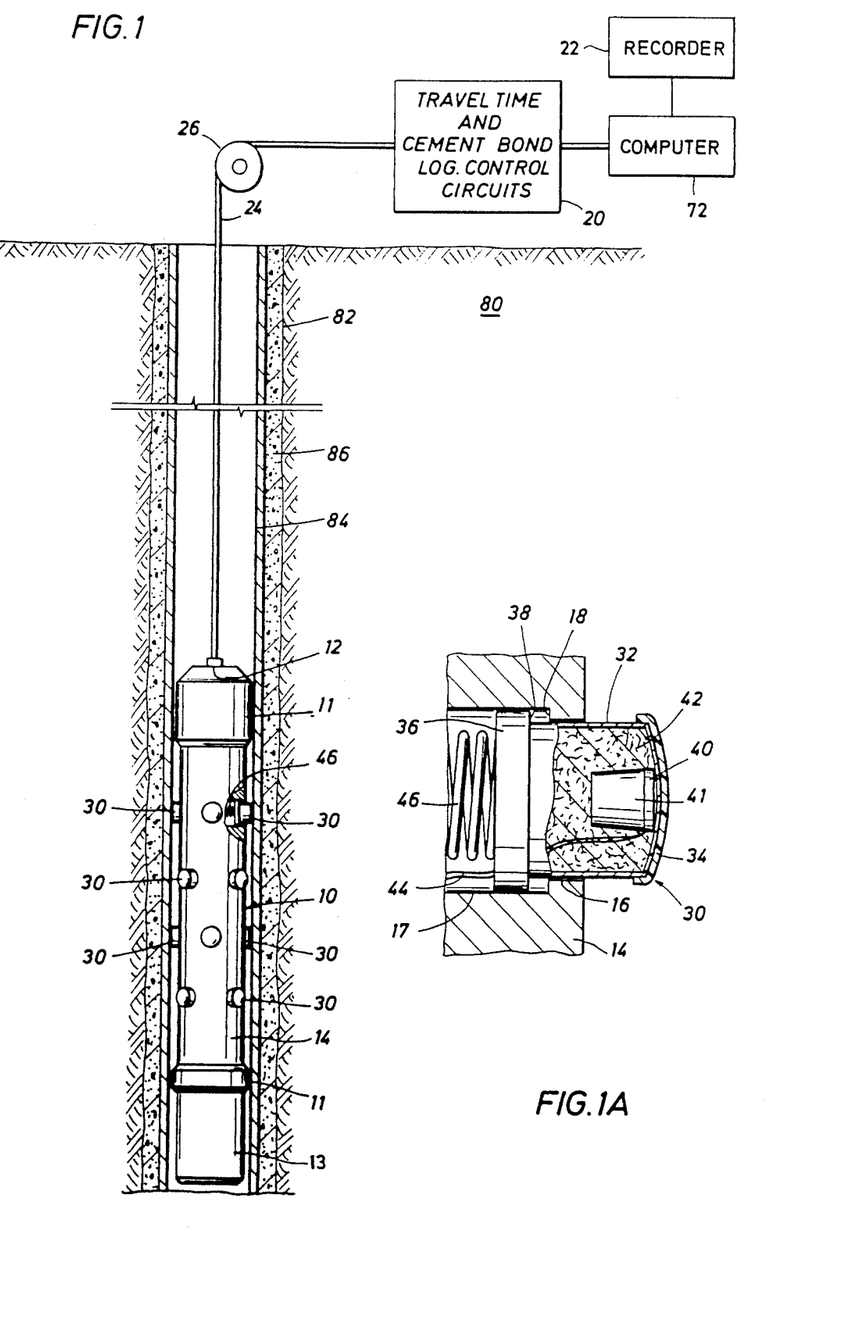
FIG. 1 is an illustration of a wireline acoustic logging tool in accord with the present invention disposed within a cemented casing in a borehole.
FIG. 1A is a cross-sectional illustration of an acoustic transducer useful in an acoustic logging tool in accord with the present invention.

FIG. 1 illustrates an acoustic logging tool 10 attached at securing means 12 to a wireline cable 24 passing over a sheave 26 to conventional surface wireline equipment (not illustrated). Disposed about the surface of the tool 10 are a plurality of transducer pads 30 which include transducer elements 40 which function as either transmitters or receivers for an acoustic pulse signal. In electrical communication with transducer elements 40 is appropriate electrical circuitry 20 to control operation of the transducers and receive and process information to provide signal amplitudes, travel time and rate of attenuation for determination of bond quality. Data is manipulated in a conventional data handling device, e.g., appropriate surface comparator circuitry or computer 72, prior to being displayed on conventional recorder 22 or other appropriate means.

The acoustic logging tool 10 is illustrated disposed in a casing 84 cemented with cement 86 to the wall of a borehole 82 in an earth formation 80. The transducer pads 30 project from the surface 14 of the tool 10 and may be forced into contact with the casing 84 by spring 46 acting on the rear thereof. Upset rings 11 or other centralizers known to those of ordinary skill in the art maintain the tool 10 centrally disposed within the casing 84.

FIG. 1A illustrates in greater detail an exemplary transducer pad 30 for use in a tool 10 in accord with the present invention. Transducer pad 30 comprises a transducer element 40 comprising a thin disk shaped member of an appropriate ceramic piezoelectric material, e.g., barium titanate, lead zirconate titanate or the like, centrally disposed within cylindrical support member 32. A large backing member 41 comprising a poor acoustical transmission medium such as tungsten loaded epoxy or the like is disposed directly behind the transducer element 40. These members are disposed and cushioned in an acoustically absorbent material 42 comprising porous rubber and the like for acoustically isolating the transducer element from the surface 14 of the tool 10. The cylindrical support 32 includes a protective member 34 of a protective material such as teflon or the like to protect the transducer element 40 from contact with the interior surface of the casing 84. The cylindrical support member 32 ends interiorly with flange 36 having surface 38 for abutting contact with surface 18 between concentric mounting bores 16 and 17 for limiting the radial travel of the transducer pad 30. A spring 46 maintains the transducer pad 30 against the interior surface of the casing 84 or fully extended with flange 36 stopped at surface 18. A similar acoustic transceiver pad is described in U.S. Pat. No. 3,811,529 at FIG. 4 which is incorporated herein by reference. Electrical contacts 44 extend from the transducer element 40 to the control circuits 20 through a central bore 48 through the tool 11.

Figure 11:
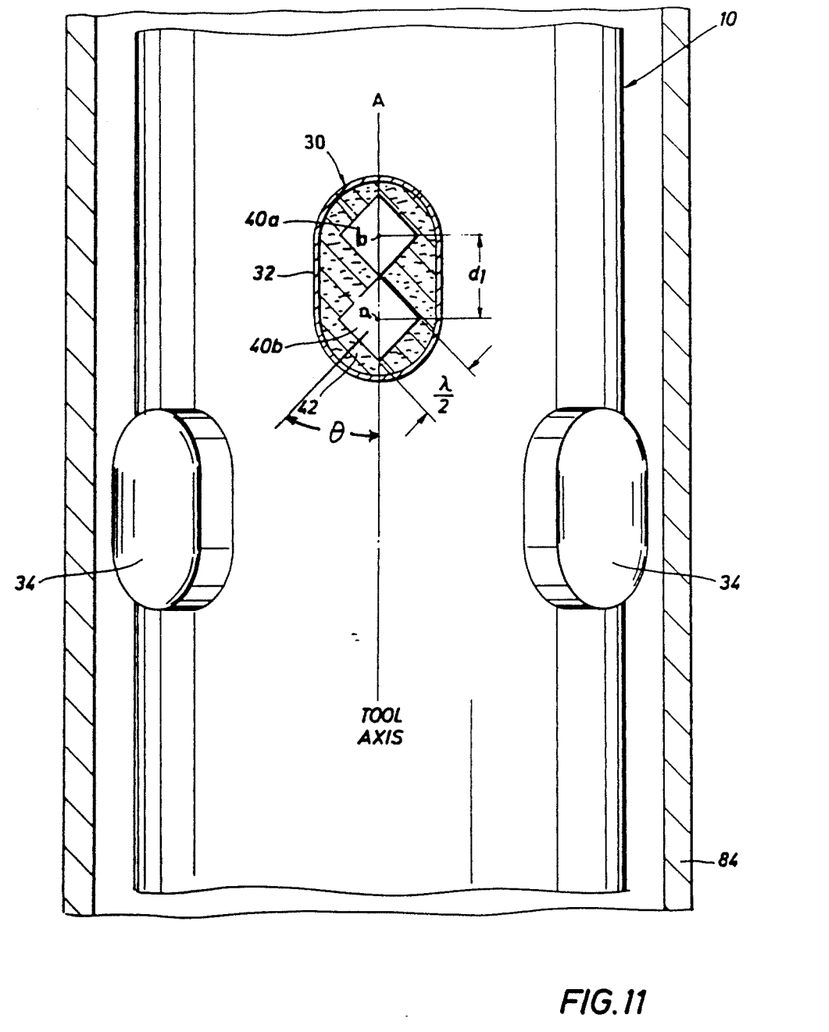
FIG. 11 is an illustration of a portion of an acoustic logging tool having directional transducer configured in accord with the present invention.

FIG. 11 illustrates a transducer pad in accord with the improved configuration of the present invention. Each transducer pad 30 comprises a pair of transducer elements 40a and 40b operated sequentially as either sequential transmitters or sequential receivers. The transducer comprises transducer elements 40a and 40b, centered at a and b, respectively, and preferably disposed along the axis of the tool 10 or the casing 84, both illustrated by line "A." The center-to-center distance between transducer elements 40a and 40b is $d_1$. The transducer elements 40a and 40b are configured and have centers positioned so that properly timed activation of the elements produces constructive interference of the acoustic pulses along the arc of investigation and destructive interference in other directions. When so disposed and activated, transducer elements 40a and 40b produce improved "steered" signals along the arc of investigation. When disposed along a line parallel to the tool axis, as illustrated in FIG. 11, the signals may easily be "steered" along the path of both the left and right helices. If disposed along a line not parallel to the tool axis, "steering" along both left and right helices is still possible after the proper delay for each direction is calculated. Although more difficult, calculation of this delay is within the skill of those in the art.

In the preferred embodiment, transducer elements 40a and 40b each include a substantially linear, leading edge disposed perpendicular to the arc of investigation and to a line connecting the transducers/receivers of the array. In the most preferred embodiment, the transducer elements are square with sides one-half the wavelength of the acoustic signal to be transmitted so that the centers a and b and the leading faces are each separated by a distance one-half the acoustic pulse wavelength along this arc. Properly timed, sequential activation of transducer elements 40a and 40b in this most preferred embodiment results in maximization of the signal strength at angle $\theta$, also the pitch of the helix and the angle of the arc of investigation in FIG. 11. In this most preferred embodiment, where the pitch of the helix of the transducer configuration is 45° and the angle between the tool axis and the line connecting the centers a and b of the transducer elements 40a and 40b is zero, this configuration maximizes the signal strength at ±45° to produce improved results. The firing of the transducer element closest to the receivers, in the illustration transducer element 40a for receivers 34 or transducer element 40b for receivers (not illustrated) located above transducer pad 30, is delayed by a time factor $t_d = d_2/V_s$ where $d_2$ is the distance along the arc of investigation between perpendiculars dropped from the centers a and b of the transducer elements. Specifically, $$t_d = \frac{d_1 \cdot \cos\theta}{V_s}$$

where
- $t_2$ = the time delay between the firing of transducer elements 40a and 40b;
- $d_1$ = the center-to-center distance between transducer elements 40a and 40b;
- $V_s$ = the speed of the acoustic wave in the arc of determination in the casing or formation; and
- $\theta$ = the angle between the line connecting the centers a and b of the transducer elements 40a and 40b and the arc of investigation.

Figure 12:
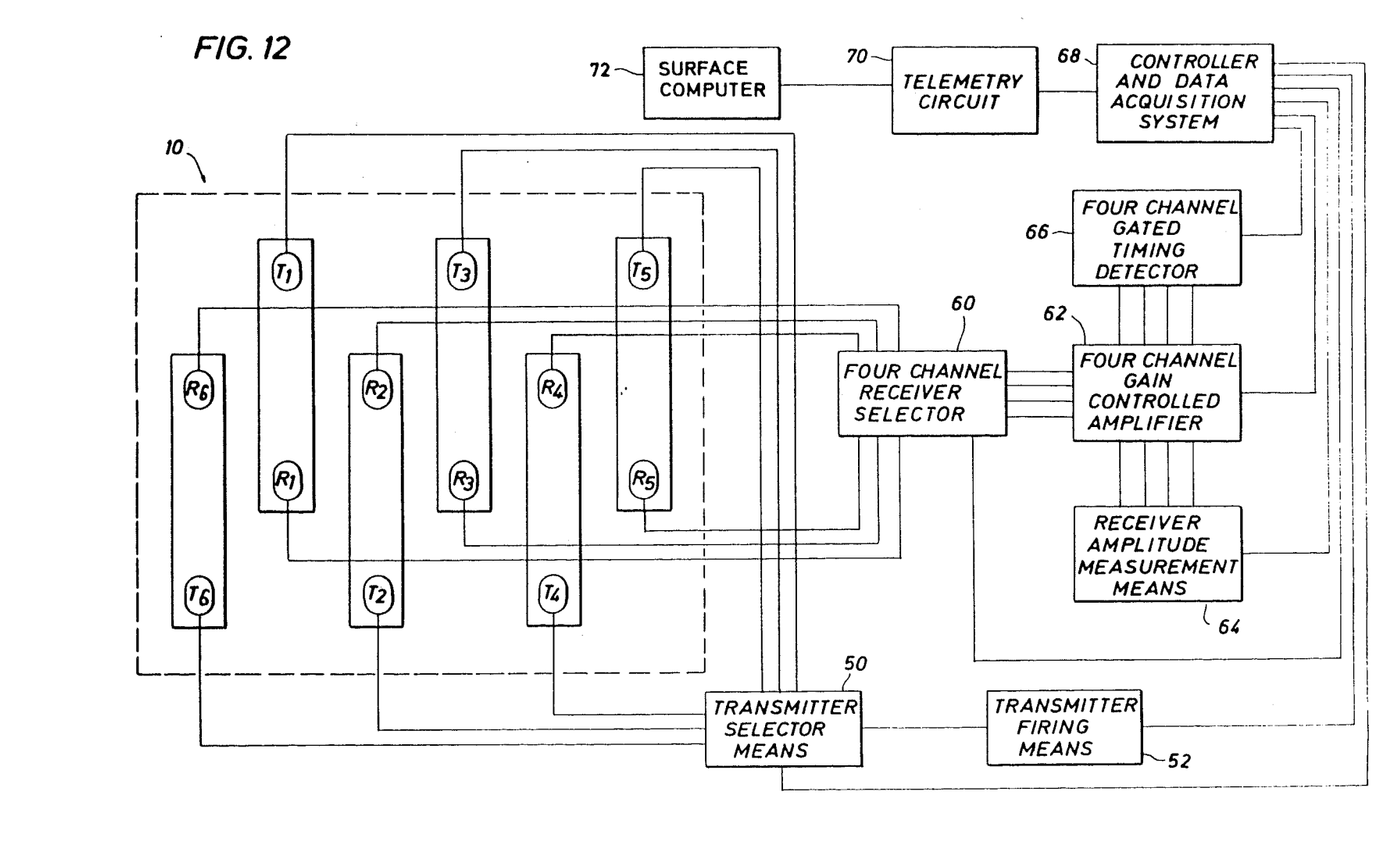
FIG. 12 is a block diagram of the major components and circuits of an acoustic logging tool in accord with the present invention.

FIG. 12 illustrates in schematic and block diagram form the major circuits and functions of the present invention. Selection of the transmitters to be activated as each transmitter pair is achieved through transmitter selector means 50 with signal activation controlled by transmitter firing means 52. Selection of the pair of receivers to be activated in conjunction with each activated transmitter is achieved through channel receiver selector 60. The received signal is processed through gain control amplifier 62 to receiver amplitude measurement means 64 and gated timing detector 66. Input and output to and from these circuit control devices is controlled by controller and data acquisition system 68. Finally, signals may be transmitted to and from the controller and data acquisition system 68 over conventional telemetry system 70 from surface computer 72. Signals telemetered to the surface are analyzed and stored in conventional data handling devices, e.g., computer 72 prior to display on recorder 22. The above-described control circuitry employs conventional circuits and subcircuits well known to those skilled in the art and, accordingly, need not be further detailed herein.

In its two most primitive embodiments, an acoustic logging tool useful with the present invention includes five or six transducers symmetrically located in a single plane perpendicular to the axis of the tool 10 and disposed equidistantly about its surface 14 at the vertices of a pentagon or a hexagon, respectively. It could also be said that these transducers are located along the arc of helix of 360° and having a pitch of zero. A pentagonal configuration provides five arrays of four equidistantly disposed transducers for providing information concerning each of five sectors comprising 72° about the circumference of the casing. In the hexagonal configuration, six transducer arrays provide similar information concerning each of six equal 60° sectors disposed about the circumference. However, in reality, such planar distribution of transducers is difficult to achieve because of the crowding resulting from attempting to place five or six transducers in a single plane in a tool whose diameter is restricted for passage through a borehole. Accordingly, Applicants have devised several preferred embodiments for disposition of a minimal plurality of transducers to produce the desired results.

Figure 6:
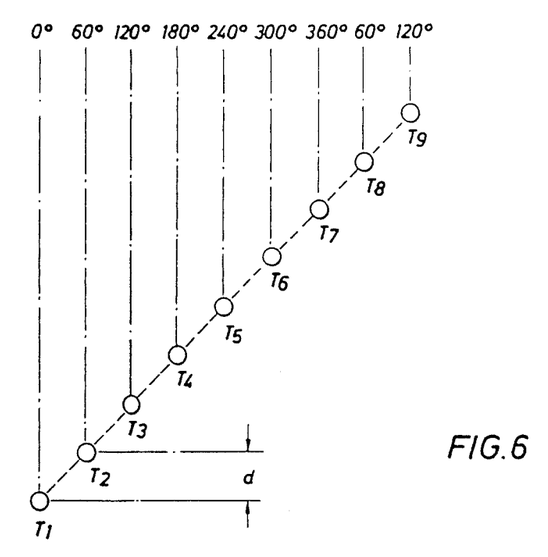
FIG. 6 is an illustration of a projection of a transducer pattern of a single helix of 480° about an acoustic logging tool in accord with the present invention.

FIG. 6 relates to one such configuration wherein nine transducers are disposed equidistantly along a single helix of 480° about the longitudinal axis of the tool 10. FIG. 6 illustrates the array pattern which would be produced by such a configuration. Where the central pair of any four adjacent transducers functions as receivers and the exterior transducers function as transmitters, the tool which would produce the pattern in FIG. 6 would provide information concerning the bond quality between transducers $T_2$ and $T_3$ with the array comprising transducers $T_1$-$T_4$. Similarly, information concerning the bond quality between transducers $T_3$ and $T_4$ would be obtained employing the array comprising transducers $T_2$-$T_5$ and so on until information concerning the bond quality between transducers $T_7$ and $T_8$ is provided by the array comprising transducers $T_6$-$T_9$. Those skilled in the art will readily comprehend that other configurations, e.g., the RTTR and TTRR configurations illustrated in the summary may be employed in place of the just described TRRT configuration to provide information concerning each sector about the circumference of the casing. Further, those skilled in the art will appreciate the transducers need not be spaced apart by 60° and that closer spacing of a greater number of transducers along a helix of greater pitch would permit determination of bond quality in appropriately narrower arcs about the circumference of the casing. However, it should be noted that the distance between adjacent transducers should be maintained preferably at least as great as $3\lambda$ where $\lambda$ is the wavelength of the acoustic signals in order to produce satisfactory results. Additionally, because the wavelength should not exceed $4t_h$ where $t_h$ is the thickness of the casing, the spacing between adjacent transducers should not be less than $12t_h$. Because $t_h$ for conventional casing is one-fourth inch to one-half inch, the spacing between adjacent transducers should typically not be less than six inches.

Figure 7:
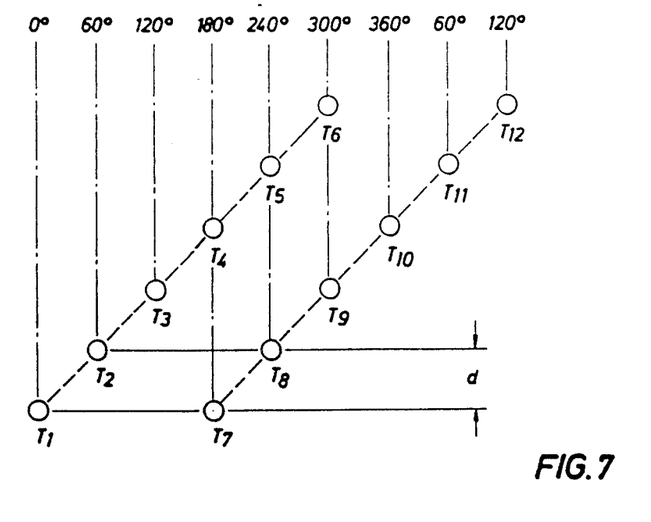
FIG. 7 is an illustration of a projection of a transducer pattern of two helices, each helix of 300° and displaced 180° about an acoustic logging tool in accord with the present invention.

FIG. 7 illustrates an alternative transducer configuration employing twelve transducers $T_1-T_{12}$ disposed in two helices of 300° each about the surface of a tool 10. The transducers are used both as transmitters and receivers. The helices are displaced 180° from one another about the surface 14 of the tool 10. Measurements are made similar to those discussed in relation to the single helix having nine transducers. In this configuration, the bond quality between $T_2$ and $T_3$, $T_3$ and $T_4$, and $T_4$ and $T_5$ is determined employing the transducers $T_1-T_6$ of the first helix and the bond quality between $T_8$ and $T_9$, $T_9$ and $T_{10}$, and $T_{10}$ and $T_{11}$ is obtained employing the transducers $T_7-T_{12}$ of the second helix. In this configuration, two transducers are mounted diametrically in each of six planes perpendicular to the axis of the tool 10 to provide information concerning each of six equidistant segments about the casing in a shorter vertical distance.

FIGS. 2-5 illustrate a configuration of twelve transducers disposed in three helices each of 180° and displaced by 120° about the surface of a tool 10. Such a configuration actually produces four transducers lying on a single arc of each of three left and three right helices such that each helix is employed to determine the bond quality in one of six sectors about a surrounding casing. This configuration provides information restricted within a narrow vertical range d. In this configuration, each array comprises the two receivers and two transmitters found along each diagonal line of FIG. 2. The measurements are made between adjacent receivers as illustrated by the solid lines of FIG. 2.

Figure 2:
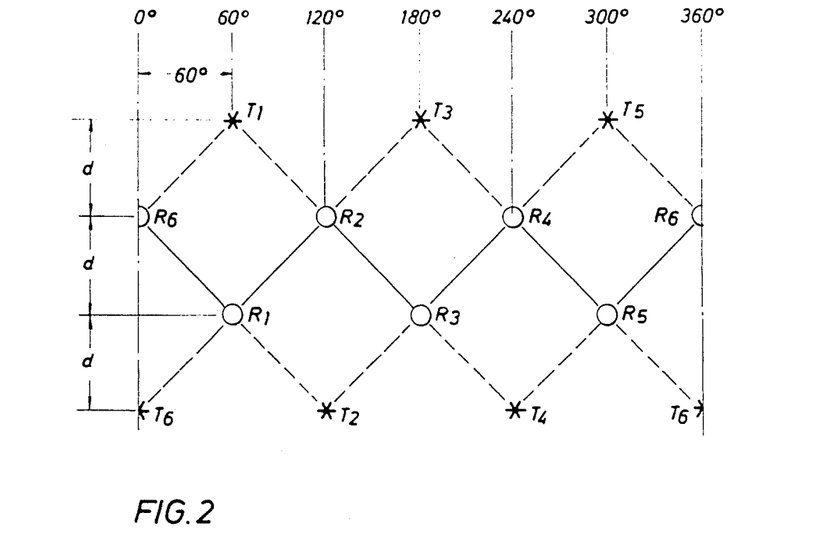
FIG. 2 is an illustration of a projection of a transducer pattern of a triple helix, each helix of 180° displaced 120° about an acoustic logging tool in accord with the present invention.
Figure 3:
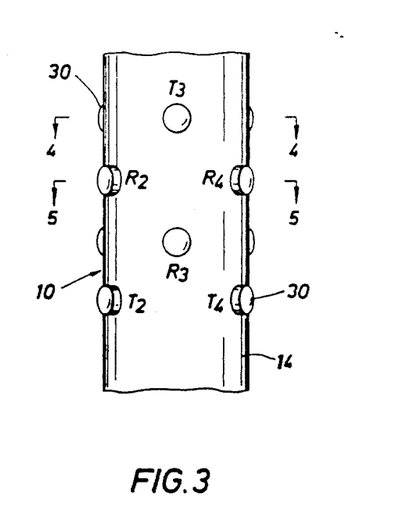
FIG. 3 is an illustration of a portion of the exterior of an acoustic logging tool in accord with the present invention and which would produce the transducer array pattern of FIG. 2.
Figure 4:
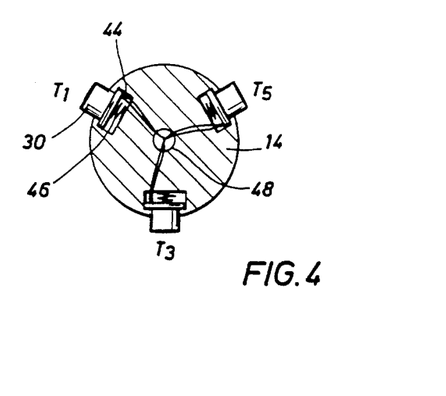
FIG. 4 is a cross-sectional illustration of the acoustic logging tool of FIG. 3 through the line 4—4.
Figure 5:
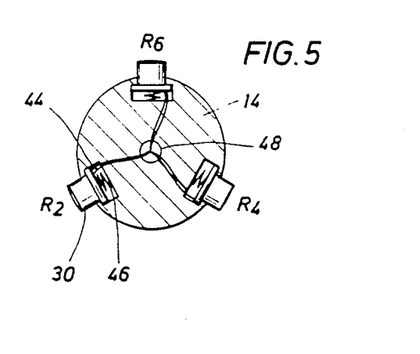
FIG. 5 is a cross-sectional illustration of the acoustic logging tool of FIG. 3 through the line 5—5.

A test device having transmitters $T_1$ and $T_2$ and receivers $R_1$ and $R_2$, in the pattern TRRT, was constructed wherein the transducers were configured about a 180° helix, each separated by 60° and with a vertical distance d of 6 inches in accord with the configuration shown in FIGS. 2 and 3. The axes of the two transmitters were at 180° with respect to each other and the measuring arc of the array is the arc between the two receivers $R_1$ and $R_2$.

In use, $T_1$ transmitted an acoustic pulse signal in the surrounding casing producing a signal first at $R_1$ and later at $R_2$. The maximum amplitude of the signal received first at $R_1$ and later at $R_2$ was measured and recorded. $T_2$ was then employed to transmit a similar signal which was received and measured first at $R_2$ and then at $R_1$. Further, the time for the signal to travel between $R_1$ and $R_2$ was measured for either one or both of the acoustic compression waves. The attenuation rate is determined by the equation:

$$a_{12} = \frac{20 \log \left( \frac{A_{11}A_{22}}{A_{12}A_{21}} \right)}{V_s(t_{12} + t_{21} - t_{11} - t_{22})}$$

where
$d_{12}$ = the attenuation rate between $R_1$ and $R_2$;
$V_s$ = the speed of the acoustic wave in the casing;
$A_{ij}$ = the amplitude of the signal received at $R_j$ from transmitter $T_i$ where i = 1 or 2 and j = 1 or 2; and
$t_{ij}$ = the time at which the signal from $T_i$ is received at $R_j$ where i = 1 or 2 and j = 1 or 2.

Figure 13:
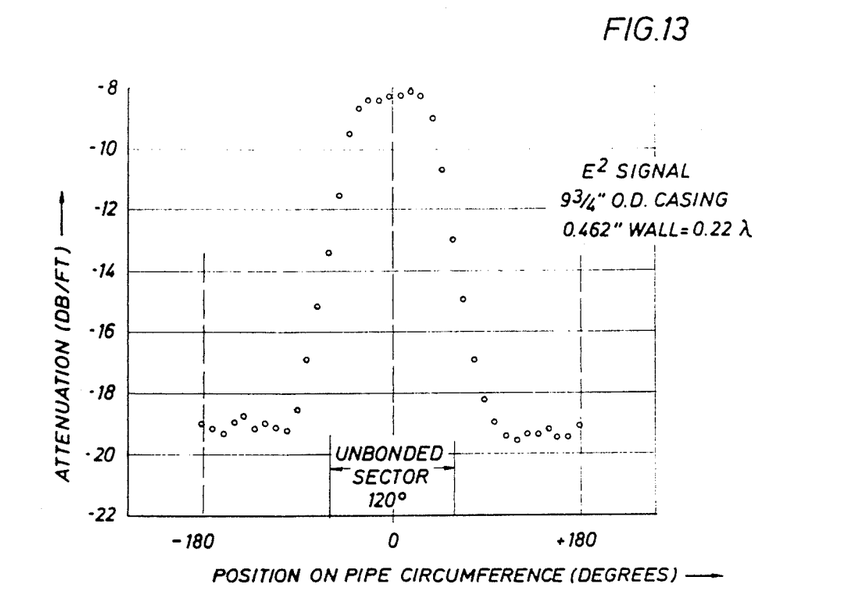
FIG. 13 is a graphical illustration of the attenuation observed in a test casing having a cement void in an arc approximately 120° wide and centered at the designated position zero.
Figure 14:
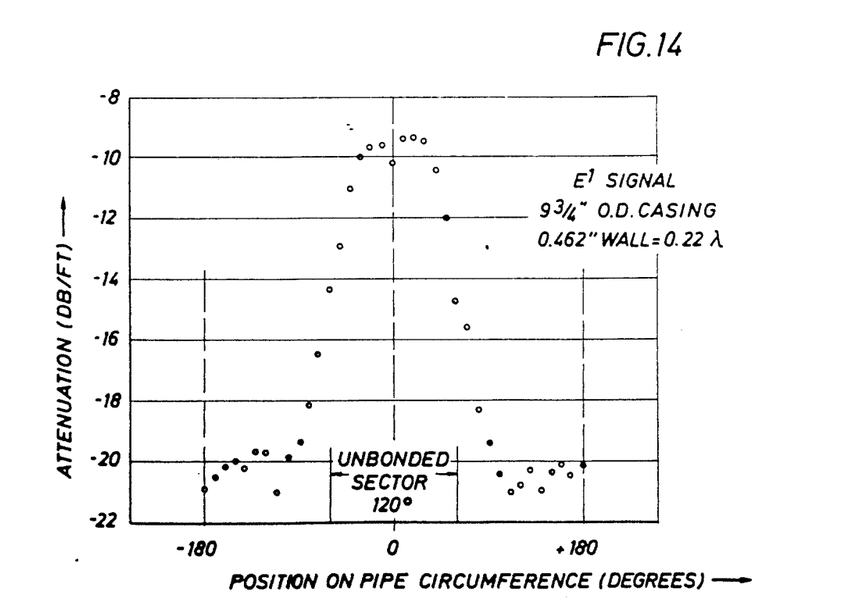
FIG. 14 is a graphical illustration of the attenuation observed in a test casing having a cement void in an arc approximately 120° wide and centered at the designated position zero.

The above device was tested in a simulated borehole wherein casing was cemented with hydrolite to a simulated borehole wall. The casing was $9\frac{3}{4}''$ OD conventional casing having a wall thickness of 0.462 inches or 0.22 where was the wavelength of the acoustic pulse signal. A void representative of a 120° unbonded sector was produced about a zero reference point. This model was placed in a water filled tank and measurements were made in an area encompassing the unbonded sector and 60° on either side thereof. Data was obtained at 10° intervals around the pipe periphery and attenuation for the maximum signal $E^1$ and the secondary signal $E^2$ plotted to produce the results illustrated in FIGS. 14 and 13, respectively. The striking feature of these curves is the symmetric attainment of minimal attenuation at points corresponding to the void or an arc of the pipe having bad bond quality.

Figure 15:
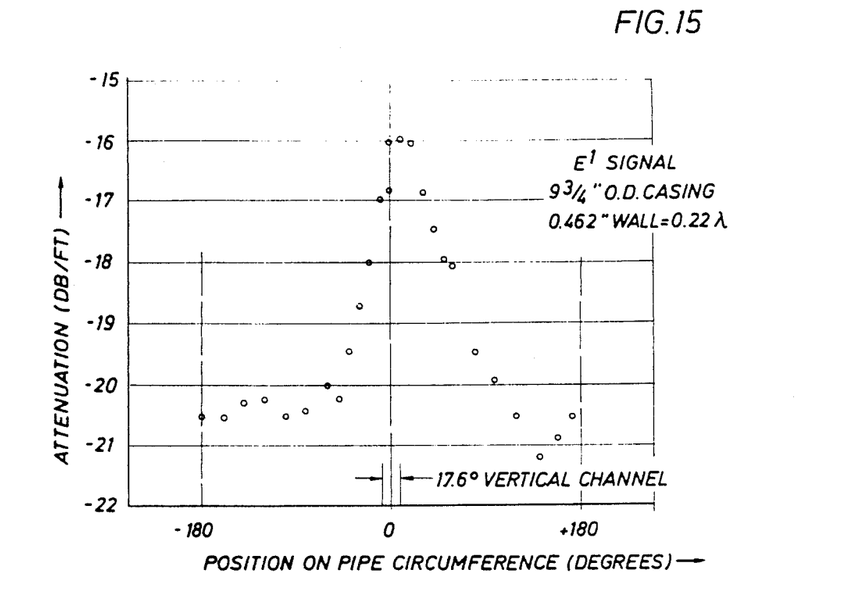
FIG. 15 is a graphical illustration of the attenuation observed in a test casing having a cement void in an arc approximately 17.6° wide and centered at the designated position zero.
Figure 16:
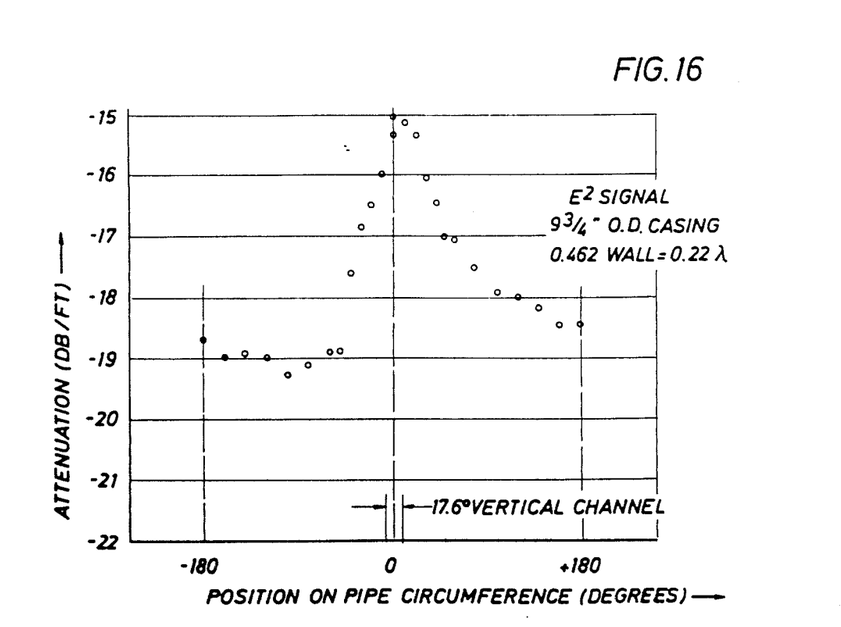
FIG. 16 is a graphical illustration of the attenuation observed in a test casing having a cement void in an arc approximately 17.6° wide and centered at the designated position zero.

A similar test was undertaken with a test annulus having a void representative of a 17.6° vertical channel at reference point zero. All other conditions were identical. The results of the measured attenuation are illustrated in FIGS. 15 and 16 showing a significant measurable attenuation difference most pronounced at the narrow vertical channel.

Figure 17:
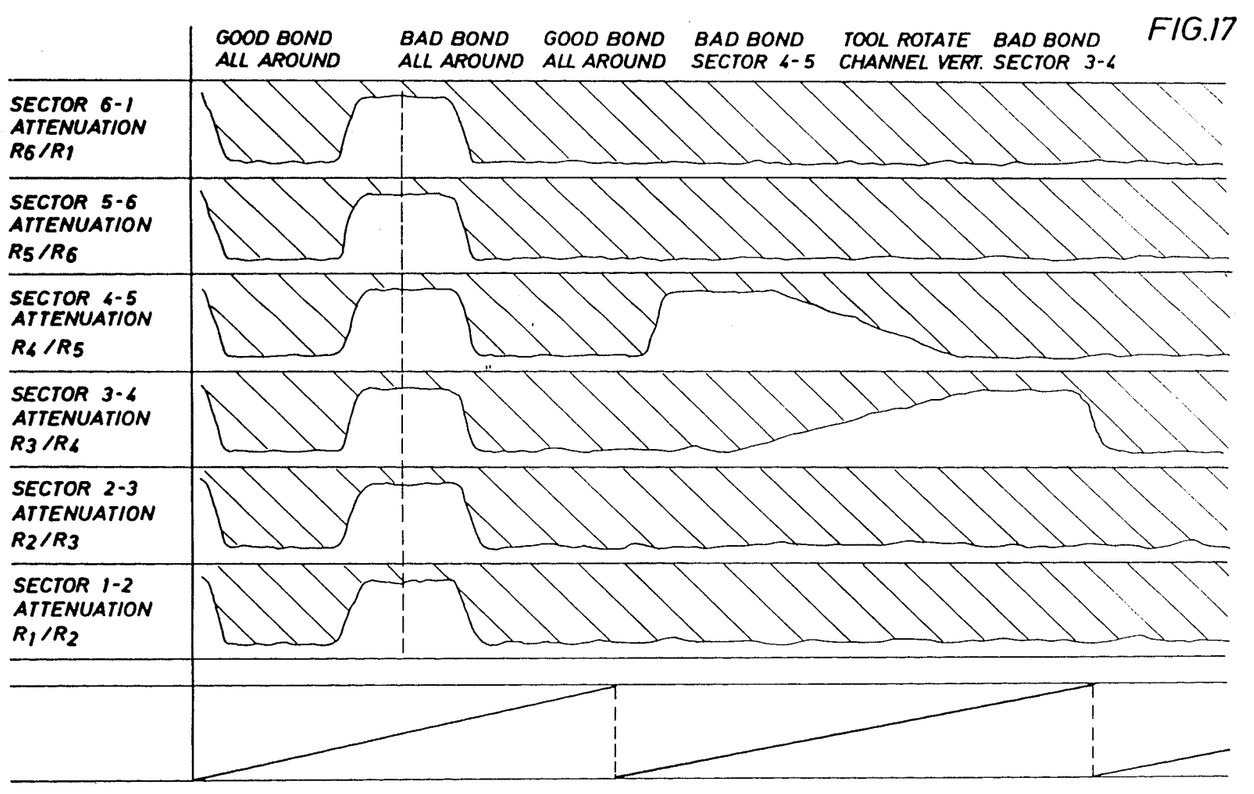
FIG. 17 is a graphical illustration of an output signal for an acoustic logging tool in accord with the present invention producing results for six sectors forming a circumference about the casing and illustrating various bond characteristics.

The incorporation of such a device in a wireline acoustic logging tool employing a conventional strip chart recorder 22 could result in easily readable output such as that illustrated in FIG. 17. Conventional depth and azimuth devices 13 would provide the operator with the depth of each measurement and the azimuthal location of each of sectors 1-2, 2-3 through 6-1. Such a device can easily indicate whether the casing and cement have formed a good bond about the entire periphery of the casing or whether a bad bond exists in one or more of the measured sectors thereabout.

Figure 8:
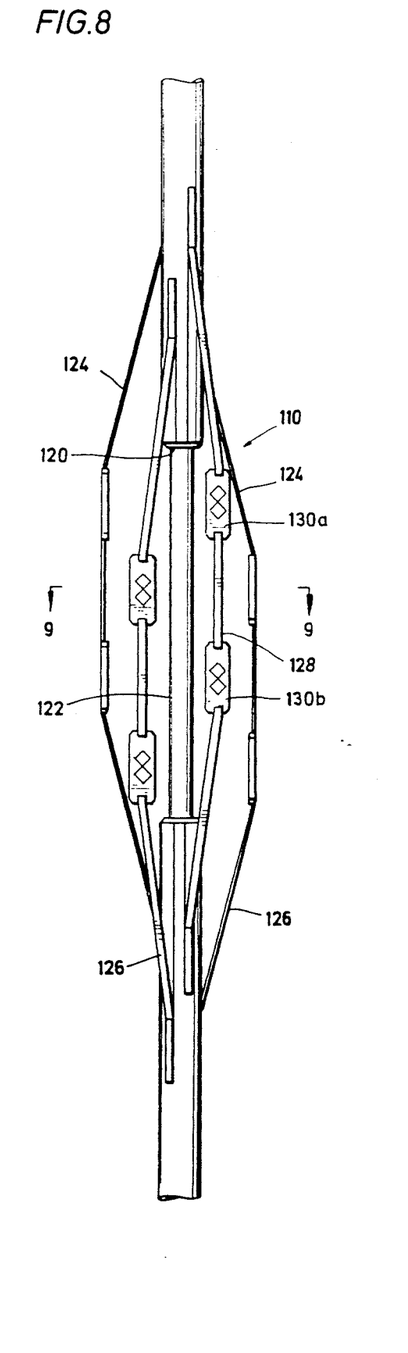
FIG. 8 is a side illustration of a presently preferred embodiment of a wireline acoustic logging tool in accord with the present invention.
Figure 9:
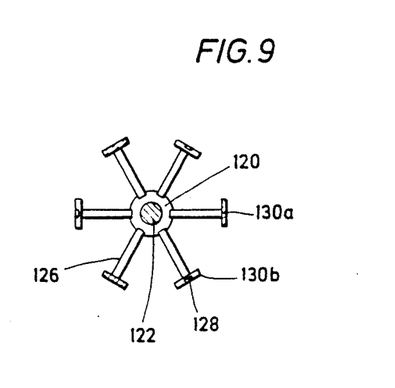
FIG. 9 is a cross-sectional illustration of the acoustic logging tool of FIG. 8 through the line 9—9.
Figure 10:
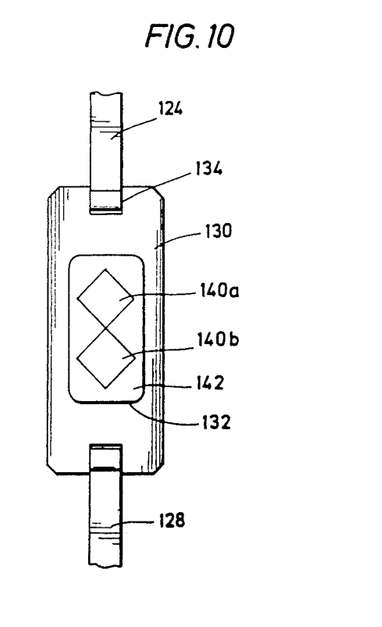
FIG. 10 is an illustration of an acoustic transducer pad of the wireline logging tool of FIG. 8.

The tool illustrated in FIGS. 8-10 is the presently preferred embodiment of a wireline tool in accord with the present invention. Tool 110 includes twelve adjustably positionable transducer pads 130 disposed in the pad configuration illustrated in FIG. 2. Tool 110 includes six adjustable arms, each arm including two transducer pads 130 separated by a spacer bar 128. Each arm further includes an upper arm 124 hingedly affixed to the central body portion 120 of the tool 110 at its upper end and hingedly affixed at 134 to the upper transducer pad 130a. A similar lower arm 126 is hingedly affixed at its lower end to the central tool portion 120 and hingedly affixed at its upper end to the bottom of lower pad 130b. Either one or both of arms 124 and 126 are slidable along central portion 120 of the tool 110 to permit a slidable ring and motor (not shown) to push and pull the arms along the central portion 120 of the tool 110 to extend or retract, respectively, the transducer pads 130. In the retracted position, the pads 130 are pulled flush against the central tool portion 120 within insets 122 to provide a tool more easily pulled through the casing. Extension of the arms carrying transducer pads 130 places the transducer elements 140a and 140b mounted within an absorbent material 142 to be brought into near contact with the inner wall of the casing to be tested.

The foregoing description of the invention has been directed in primary part to a particular preferred embodiment and method in accordance with the requirements of the patent statutes and for purposes of explanation and illustration. It will be apparent, however, to those skilled in the art that many modifications and changes in the specifically described apparatus and method may be made without departing from the scope and spirit of the invention. For example, Applicants have illustrated and described a device and method employing a plurality of transducers each having two transducer elements equidistantly spaced along one or more helices. However, those skilled in the art would be aware that a plurality of transducer elements spaced and properly sequentially activated may be employed to further maximize the directional signal strength. Applicants believe the disclosed apparatus and method provide the most compact, efficient and economical device in accord with the present invention. However, those skilled in the art will appreciate that other configurations having the described characteristics may produce the same results. Therefore, the invention is not restricted to the particular form of construction and method illustrated and described, but covers all modifications which may fall within the scope of the following claims.

It is Applicants' intention in the following claims to cover such modifications and variations as fall within the true spirit and scope of the invention.

What is claimed is:

1. An acoustic logging tool useful for determining the quality of a bond between a wall of a borehole penetrating an earth formation and a casing cemented therein in several adjacent sectors around the casing, comprising:
   a sonde, including means for securing said sonde to a wireline;
   a plurality of pads extendable from said sonde, each said pad having an exterior surface for contacting a casing surrounding said sonde;
   a plurality of transducers for transmitting and receiving acoustic pulse signals into said casing, said plurality of transducers disposed in said exterior surfaces of said plurality of pads;
   means for selecting a plurality of arrays of transducers, each array comprising four transducers disposed circumferentially on an arc projected through at least four of said pads, two said transducers functioning as transmitters and two functioning as receivers; and
   means for determining the bond quality in each said sector between two adjacent transducers in each said array employing the compensated attenuation of the compressional acoustic pulse signals received by said two receivers from said two transmitters.

2. The acoustic logging tool of claim 1 further comprising means for determining the travel time of said compressional acoustic pulse signals between said adjacent transducers.

3. The acoustic logging tool of claim 2 further comprising means for determining the position within said borehole of each sector defined by said adjacent transducers.

4. The acoustic logging tool of claim 3 further comprising means for centralizing said sonde within said borehole.

5. The acoustic logging tool of claim 4 further comprising means for transmitting data from said tool to a remote location at the surface and means for displaying an output indicative of the bond quality in each said sector.

6. The acoustic logging tool of claim 1 wherein adjacent transducers are separated by a distance at least as great as $3\lambda$ where $\lambda$ is the wavelength of said compressional acoustic pulse signal.

7. The acoustic logging tool of claim 6 wherein adjacent transducers are separated by a distance at least as great as $12t_h$ where $t_h$ is the thickness of said casing.

8. The acoustic logging tool of claim 1 wherein the wavelength of said compressional acoustic pulse signal is at least as great as $4t_h$ where $t_h$ is the thickness of said casing.

9. The acoustic logging tool of claim 1 wherein each said array comprises first and second transmitters $T_1$ and $T_2$ and first and second receivers $R_1$ and $R_2$ disposed in an order so that at least one pair of like functioning transducers are adjacent.

10. The acoustic logging tool of claim 1 wherein each said transducer comprises first and second transducer elements and means for activating sequentially said first and second transducer elements to maximize the transmitted acoustic pulse signal along said arc.

11. The acoustic logging tool of claim 10 wherein said first and second transducer elements of each transducer are disposed with centers defining a line parallel to the axis of said sonde.

12. The acoustic logging tool of claim 11 wherein said centers of said first and second transducer elements of each transducer are separated by a distance d and wherein said means for sequentially activating delays the sequential activation of said elements by a delay time $t_d = (d/V_s) \cos \theta$ where $V_s$ is the acoustic velocity of said compressional acoustic pulse signal in said casing and $\theta$ is the angle between said sonde axis and said arc.

13. An acoustic logging tool useful for determining the presence of fractures in a borehole penetrating an earth formation, comprising:
   a sonde, including means for securing said sonde to a wireline;
   a plurality of pads extendable from said sonde, each said pad having an exterior surface for contacting the wall of a borehole surrounding said sonde;
   a plurality of transducers for transmitting and receiving acoustic pulse signals into said wall, said plurality of transducers disposed in said exterior surfaces of said plurality of pads;
   means for selecting a plurality of arrays of transducers, each array comprising four transducers disposed circumferentially on an arc projected through at least four of said pads, two said transducers functioning as transmitters and two functioning as receivers; and
   means for determining the presence of a fracture in a sector of said borehole wall between two transducers in each said array employing the compensated attenuation of the shear acoustic pulse signals received by said two receivers from said two transmitters.

14. A method for detecting the quality of a cement bond between a wall of a borehole penetrating an earth formation and a casing cemented therein, said bond quality detected behind an arc of said cemented casing defined by first and second circumferentially separated points, comprising:
   transmitting an acoustic compression wave through said casing along said arc;
   measuring the amplitude of said acoustic compression wave received at each of two receivers, said two receivers defining said first and second circumferentially separated points;
   measuring the time for said acoustic compression wave to travel between said adjacent receivers; and determining the cement bond quality from the rate of attenuation of said compression wave between said receivers.

15. The method of claim 14 further comprising displaying said rate of attenuation as an indication of the quality of the cement bond along the arc defined by said first and second circumferentially separated points.

16. The method of claim 14 further comprising determining the location within said borehole of said arc between said circumferentially separated points.

17. The method of claim 16 wherein determining said position comprises determining the depth of said arc within said borehole and determining the azimuthal location of said arc within said borehole.

18. A method for detecting the presence of fractures in a wall of a borehole penetrating an earth formation in an arc of said borehole wall defined by first and second circumferentially separated points, comprising:
  transmitting an acoustic shear wave through said wall of said borehole along said arc;
  measuring the amplitude of said acoustic shear wave received at each of two receivers, said two receivers defining said first and second circumferentially separated points;
  measuring the time for said acoustic shear wave to travel between said receivers; and
  detecting the presence of fractures between said first and second points from said measured amplitudes and said measured time by determining the rate of attenuation of said shear wave between said receivers.

19. An acoustic logging tool useful for determining the quality of a bond between a wall of a borehole penetrating an earth formation and a casing cemented therein behind an arc of said casing defined by two circumferentially separated points $R_i$ and $R_j$, comprising:
  an elongated housing, including means for securing said housing to a wireline;
  nine transducers for transmitting and receiving acoustic pulse signals, said transducers disposed equidistantly about the circumference of said housing in a single helix of 480°;
  means for operating said transducers in six different arrays, each said array comprising four said transducers disposed along a single arc of said helix, two said transducers $T_i$ and $T_j$ capable of transmitting and two different said transducers $R_i$ and $R_j$ capable of receiving an acoustic pulse signal, said transducers disposed so that the distance between $T_i$ and $R_i$ is less than the distance between $T_i$ and $R_j$ and the distance between $T_j$ and $R_j$ is less than the distance between $T_j$ and $R_i$;
  means for generating a first acoustic pulse signal from each said transducer $T_i$ and a second acoustic pulse signal from each said transducer $T_j$;
  means for measuring the amplitide $A_{ii}$ and $A_{ij}$ of a selected portion of said first acoustic pulse signal received at said transducers $R_i$ and $R_j$ and the amplitude $A_{jj}$ and $A_{ji}$ of a selected portion of said second acoustic pulse signal received at said transducers $R_j$ and $R_i$;
  means for determining the time $\Delta t$ for either of said acoustic pulse signals to travel between transducers $R_i$ and $R_j$; and
  means for determining the rate of attenuation $\alpha_{ij}$ of said compression wave between said receivers $R_i$, $R_j$ from said measured amplitudes $A_{ii}$, $A_{ij}$, $A_{ji}$, $A_{jj}$ and said travel time $\Delta t$.

20. An acoustic logging tool useful for determining the quality of a bond between a wall of a borehole penetrating an earth formation and a casing cemented therein behind an arc of said casing defined by first and second circumferentially separated points, comprising:
  a housing, including means for securing said housing to a wireline;
  transducers for transmitting and receiving acoustic pulse signals into a casing surrounding said housing, said transducers disposed about the outer surface of said housing;
  means for operating said transducers in a plurality of different arrays, each said array comprising four transducers disposed along a single arc about the circumference of said housing, each said array comprising first and second transducers capable of transmitting and first and second transducers capable of receiving an acoustic pulse signal, said transducers disposed so that an adjacent pair of transducers in said array perform the same function in said array;
  means for generating a first acoustic pulse signal from said first transmitting transducer and a second acoustic pulse signal from said second transmitting transducer;
  means for measuring the amplitude of a selected portion of said first acoustic pulse signal received at each of said first and second receiving transducers and the amplitude of a selected portion of said second acoustic pulse signal received at each of said first and second receiving transducers; and
  means for determining the time for either of said acoustic pulse signals to travel between said adjacent pair of transducers.

21. The apparatus of claim 20 further comprising:
  means for computing the rate of attenuation of said acoustic pulse signals between said adjacent pair of transducers from said measured amplitudes and said travel time.

22. The apparatus of claim 21 further comprising means for displaying said rate of attenuation.

23. The apparatus of claim 21 further comprising means for comparing said computed attenuation with an attenuation indicative of a good cement bond between said casing and said earth formation.

24. The apparatus of claim 20 wherein adjacent transducers on said arc are separated by a distance at least as great as $3\lambda$ where $\lambda$ is the wavelength of said acoustic pulse signals.

25. The apparatus of claim 24 wherein adjacent transducers on said arc are separated by a distance at least as great as $12t_h$ where $t_h$ is the thickness of said casing.

26. The apparatus of claim 25 wherein the wavelength of said acoustic pulse signals is at least as great as $4t_h$.

27. The apparatus of claim 20 comprising at least six transducers equidistantly disposed about the circumference of said housing.

28. The apparatus of claim 27 wherein said transducers are disposed helically about said housing.

29. The apparatus of claim 27 comprising nine transducers disposed about said housing in a single helix.

30. The apparatus of claim 27 comprising twelve transducers disposed in two helices of six transducers each about said housing wherein said transducers are disposed in six planes perpendicular to the axis of said housing, each plane including a single transducer for each helix disposed diametrically to each other.

31. The apparatus of claim 27 comprising twelve transducers disposed in three helices of four transducers each about said housing wherein said transducers are disposed in four planes perpendicular to the axis of said housing, each plane including a single transducer for each helix disposed 120° from each other.

32. The apparatus of claim 20 further comprising means for extending each of said transducers radially from said surface of said housing.

33. The apparatus of claim 20 wherein said transducers are separated on said arc by less than 90°.

34. The apparatus of claim 20 further comprising means for determining the azimuth of said borehole.

35. The apparatus of claim 20 comprising a plurality of said arrays of transducers to permit determining of a bond quality for each of a plurality of arcs, said plurality of arcs forming in combination a circumference of said casing.

36. A method for detecting the quality of a cement bond between a wall of a borehole penetrating an earth formation and a casing cemented therein, said bond quality detected behind an arc of a cemented casing defined by two circumferentially separated points $R_i$ and $R_j$ on said well casing, comprising:

disposing at a known depth and orientation within said cased borehole a tool having at least one array of four transducers disposed along a single arc on the surface of said tool, two transducers $T_i$ and $T_j$ capable of transmitting and two different transducers $R_i$ and $R_j$ capable of receiving an acoustic pulse signal, said transducers disposed so that the distance between $T_i$ and $R_i$ is less than the distance between $T_i$ and $R_j$ and the distance between $T_j$ and $R_j$ is less than the distance between $T_j$ and $R_i$;

generating from said tool an acoustic pulse signal at a frequency and location which produces a first acoustic compression wave transmitted through said casing from a point $T_i$ on said well casing so that said first compression wave arrives at $R_i$ prior to arriving at $R_j$;

measuring the amplitude $A_{ii}$ of a selected portion of said first acoustic compression wave in said casing received at said point $R_i$ and the amplitude $A_{ij}$ of a selected portion of said first acoustic compression wave received at said point $R_j$;

generating from said tool an acoustic pulse signal at said frequency and a location which produces a second acoustic compression wave transmitted through said casing from a point $T_j$ on said well casing so that said second compression wave arrives at $R_j$ prior to arriving at $R_i$;

measuring the amplitude $A_{jj}$ of a selected portion of said second acoustic compression wave in said casing received at said point $R_j$ and the amplitude $A_{ji}$ of a selected portion of said first acoustic compression wave received at said point $R_i$;

determining the time $\Delta t$ for either of said acoustic compression waves to travel between points $R_i$ and $R_j$;

computing the rate of attenuation $\alpha_{ij}$ for said acoustic compression wave between said points $R_i$ and $R_j$ on said casing from said measured amplitudes and travel time of said acoustic compression waves between said points $R_i$ and $R_j$; and displaying said rate of attenuation as an indicator of the quality of the cement bond behind said arc between points $R_i$ and $R_j$.

37. The method of claim 36 comprising computing said rate of attenuation from the equation $$\alpha_{ij} = \frac{10 \cdot \log\left(\frac{A_{ii}}{A_{ij}} \cdot \frac{A_{jj}}{A_{ji}}\right)}{V_s \Delta t}$$

where $V_s$ is the speed of said wave in said casing.

38. The method of claim 36 further comprising comparing said rate of attenuation with a known rate of attenuation for a bond of known quality.

39. The method of claim 36 for detecting the quality of the cement bond in each of a plurality of circumferential segments defined by points $R_i$ and $R_j$, said segments combining to form a complete circumference of said casing, comprising:

repeating the steps of claim 36 for each said segment forming said complete circumference of said casing.

40. The method of claim 36 further comprising measuring the azimuth of said borehole at said known depth in order to precisely locate points $R_i$ and $R_j$ on said casing.

41. The method of claim 40 further comprising measuring the depth of said points $R_i$ and $R_j$ in said borehole.

42. A method for detecting the quality of a cement bond between a wall of a borehole penetrating an earth formation and a casing cemented therein, said bond quality detected behind an arc of said cemented casing defined by first and second circumferentially separated points, comprising:

transmitting a first acoustic compression wave through said casing along said arc, said first acoustic compression wave arriving at said first point before arriving at said second point;

measuring the amplitude of a selected portion of said first acoustic compression wave in said casing at said first point and at said second point;

transmitting a second acoustic compression wave through said casing along said arc, said second acoustic compression wave arriving at one of said first or second points before arriving at the other of said points;

measuring the amplitude of a selected portion of said second acoustic compression wave in said casing at said first point and at said second point;

determining the time for one of said acoustic compression waves to travel between said first and second points;

computing the rate of attenuation for said acoustic compression wave between said first and second points on said casing from said four measured amplitudes and said measured travel time; and displaying said rate of attenuation as an indication of the quality of the cement bond behind said arc between said first and second points.

43. The method of claim 42 for detecting the quality of the cement bond in each of a plurality of arcs which in combination form a circumference of said casing, each arc defined by first and second circumferentially separated points, comprising:

repeating the steps of claim 42 for each said arc to provide an indication of the quality of the cement bond behind each arc of said casing.

44. The method of claim 43 further comprising measuring the azimuth of said borehole at said circumference to precisely locate said arc on said casing.

45. The method of claim 44 further comprising measuring the depth of said circumference in said borehole.

* * * * *

UNITED STATES PATENT AND TRADEMARK OFFICE
CERTIFICATE OF CORRECTION

PATENT NO. : 4,805,156
DATED : February 14, 1989
INVENTOR(S) : George Attali et al It is certified that error appears in the above-identified patent and that said Letters Patent is hereby corrected as shown below:

Column 13, Line 58, delete "amplitide" and insert therefor --amplitude--.

Signed and Sealed this

Twenty-fifth Day of July, 1989

Attest:

DONALD J. QUIGG

Attesting Officer     Commissioner of Patents and Trademarks